United States Patent [19]

Cinqualbre

[11] Patent Number: 4,710,874
[45] Date of Patent: Dec. 1, 1987

[54] METHOD AND APPARATUS FOR DISPLAYING PARTICLE SEDIMENTATION RATES IN LIQUIDS

[76] Inventor: Paul-Henri Cinqualbre, 20, rue de la Ravinelle, 54000 Nancy, France

[21] Appl. No.: 743,596

[22] Filed: Jun. 11, 1985

[30] Foreign Application Priority Data

Jun. 13, 1984 [FR] France ................................. 8409360

[51] Int. Cl.$^4$ ..................... G01N 33/48; G01N 21/51; G06F 15/42
[52] U.S. Cl. ...................................... 364/413; 356/442
[58] Field of Search ................ 364/413; 356/441, 427, 356/246, 338-339, 442, 434, 428; 250/573

[56] References Cited

U.S. PATENT DOCUMENTS

| Re. 27,866 | 1/1974 | Adler | 356/441 |
| 3,617,222 | 11/1971 | Matte | 356/427 |
| 3,830,969 | 8/1974 | Hofstein | 356/427 |
| 4,118,974 | 10/1978 | Nozaki | 356/39 |
| 4,252,438 | 2/1981 | Haing | 356/442 |
| 4,303,342 | 12/1981 | Takahashi | 356/427 |
| 4,325,910 | 4/1982 | Jordan | 356/434 |
| 4,528,159 | 7/1985 | Liston | 356/246 |

Primary Examiner—Jerry Smith
Assistant Examiner—Gail O. Hayes
Attorney, Agent, or Firm—Erwin S. Teltscher

[57] ABSTRACT

An apparatus and a method for continuous display of a particle sedimentation rate in a liquid includes a rotary support device adapted to hold a plurality of light-transparent containers, and wherein each container holds a liquid. Any container may be selected to be observed so that at least a portion of the selected container may be observed from the exterior. A light source illuminates the selected container, and an image-forming device is arranged to form an image of the aforesaid portion of the selected container, and the liquid held therein. Video signals are created from the so-formed image, and a computer is arranged to process the video signals. A transmission conduit transmits the video signals from the image-forming device to the computer, and a display is provided for displaying the signals processed by the computer.

14 Claims, 5 Drawing Figures

METHOD AND APPARATUS FOR DISPLAYING PARTICLE SEDIMENTATION RATES IN LIQUIDS

BACKGROUND OF THE INVENTION

The present invention relates to a method and an apparatus for automatically and continuously determining and displaying the sedimentation rate of particles in suspension or composing any type of liquid but more particularly a complex biological liquid.

In medical analysis laboratories, measurement of the sedimentation rate of blood is still carried out in an entirely manual fashion.

After the sample of blood is taken, the personnel place the liquid in graduated tubes maintained in a vertical or upright position on an appropriate support.

Measurement consists of noting the variation in position of the interphase or border at regular time intervals, for example every half-an-hour or every quarter-hour. At the end of the regulation time period, total duration of the measurement, the height of drop is noted and referred to the customer sheet in the form of the ratio of the height of drop in millimeters to the time elapsed, expressed in hours.

For reasons of efficacy and profitability, in all laboratories several measurements are carried out simultaneously. It is then necessary for the person concerned with these measurements conscientiously and scrupulously to note the times and the heights of drop of the most dense material: for blood, the red corpuscles.

The great attention needed for these measurements cannot always be provided because, for reasons of efficacy, personnel cannot remain in front of graduated tubes waiting for the regulation time between two positions to be measured to elapse.

Thus, over and above the drawbacks of an entirely manual measurement, the degree of efficacy in attention involved in the personal value of the operator but also the level of work load or overload all constitute a source of error and sometimes of interpretation which will call the responsibility of the laboratory into question.

SUMMARY OF THE INVENTION

The question of the invention is entirely to do away with the risks of error while completely automating measurement and recording the result. To this end, the invention relates to a method of and to the apparatus for carrying out the method in order automatically and continuously to measure the sedimentation rate of particles in suspension or composing a complex biological or other liquid, characterised in that the apparatus comprises a turning support which can be immobilised or which is already immobilised, receiving tubes of samples side by side in support housings, each position being in its bottom part, in the case of the turning support, identified by a coded label.

The apparatus likewise comprises an optical analysis assembly of the charge transfer type, a calculation module and a data module with a screen, keyboard and printer for monitoring and printing the results directly onto the customer sheet.

The method consists in detecting, at each rotation of the sample carrying support or permanently in the fixed support alternative embodiment, the variation in the level of the interphase for each tube of sample by sensitising charge transfer devices such as a bar or matrix and then analysing these variations by video means assessed by data means.

Over and above the advantages metioned hereinabove, the invention makes it possible directly to establish the result of the test and to invoice the customer. It also makes it possible to carry out an interesting number of measurements simultaneously and in any case a number of measurements sufficient to utilise the capacity of a large analytical laboratory.

Furthermore, the price envisaged for the apparatus makes it possible to envisage rapid amortisation due to the saving on time resulting from complete automation of measurements.

Furthermore, viability of the equipment and reliability of measurement avoids the need to carry out further tests in cases considered doubtful beforehand.

BRIEF DESCRIPTION OF THE DRAWINGS

The invention will be understood more clearly from reading the following description which relates to a form of embodiment of the invention by way of non-limitative example, reference being made to the accompanying drawings, in which.

Figure 1:
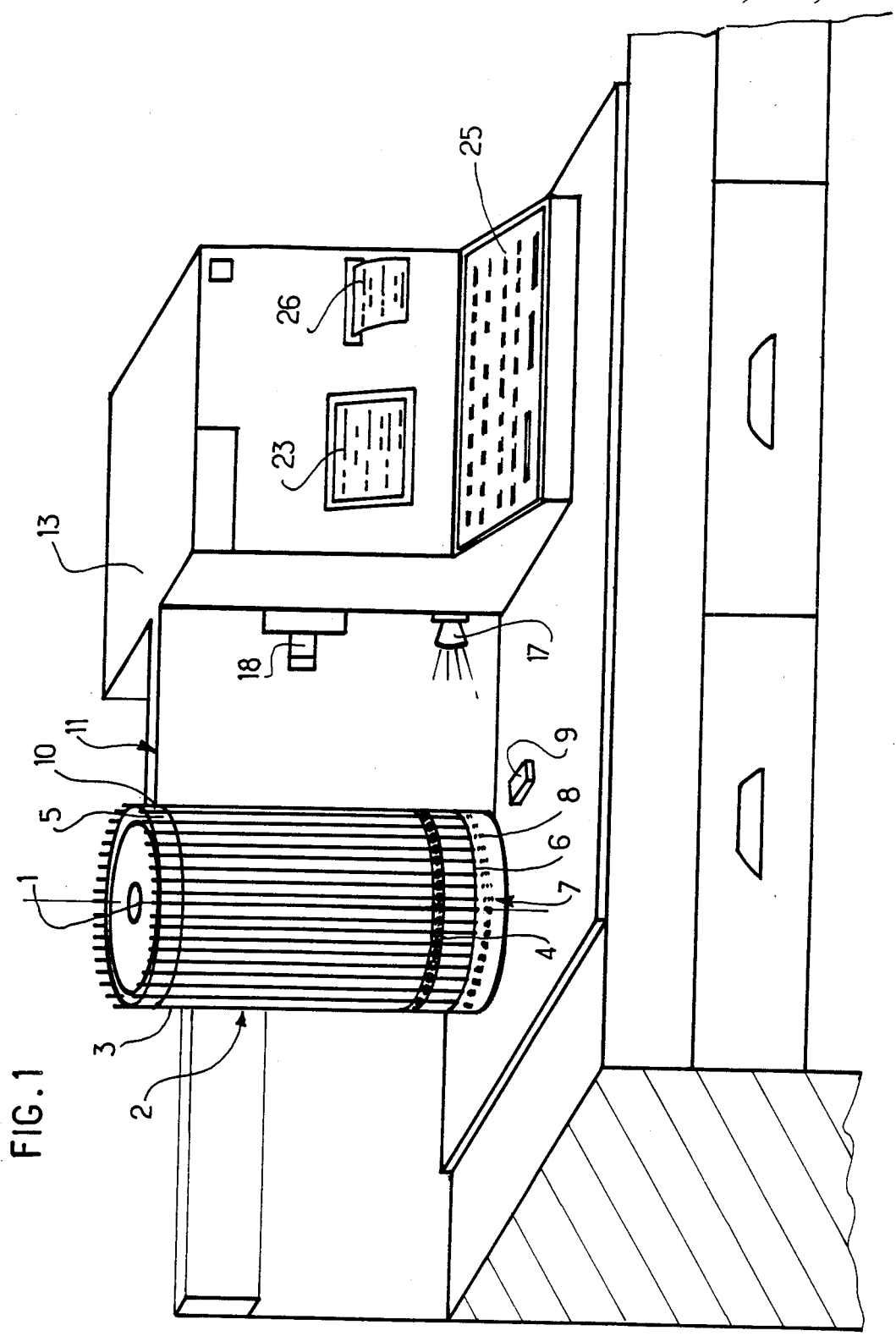
FIG. 1 is a diagrammatic overall view in perspective showing the measuring apparatus according to the invention in an embodiment which has a movable support.
Figure 2:
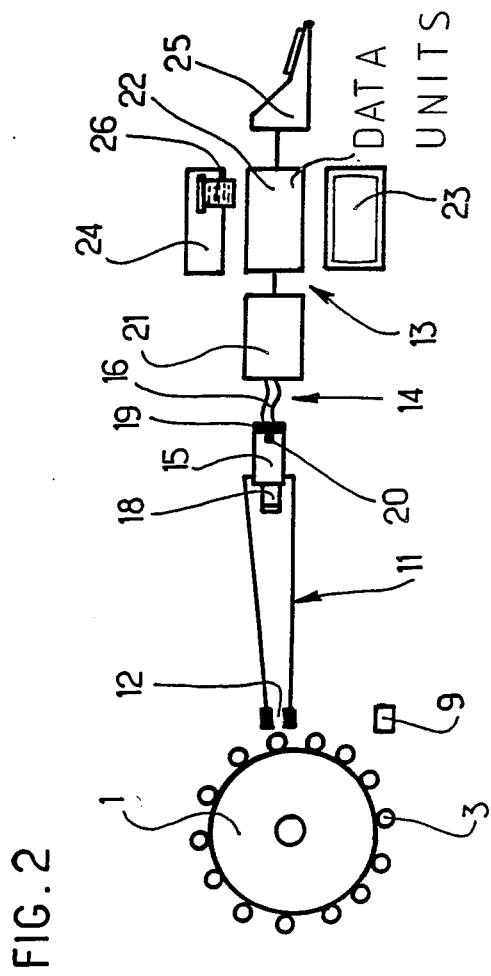
FIG. 2 is a diagrammatic horizontal section through the measuring apparatus shown in FIG. 1.

First of all, a description will be given of the measuring apparatus according to the invention in its general characteristics, reference being made to FIGS. 1 and 2 of the sheets of drawings appended and relating to the embodiment which has a rotating sample carrying support.

The apparatus according to the invention has a rotating support 1 in the form of a drum, for example, the lateral surface 2 of which is provided with means for holding containers or tubes containing the samples to be measured. These supporting means may for example take the form of a bottom ring 4 provided with circular passages, a top ring 5 which is identical and a bottom stop ring on which the bottoms of the tubes 3 can rest, so that no vertical displacement of the tubes or containers 3 occurs during rotation of the support 1. Provided underneath this ring are positions for labels 8 which carry an identification coding.

As will be seen hereinafter, the gap between tubes may be very small so as to offer a filling coefficient.

In the basic version envisaged, having a rotating support, the capacity will make it possible to meet the needs of current analytical laboratories and even larger laboratories insofar as, in terms of internal organisation, staggering of blood samples will ensure a complete capacity turn round of about two hours.

The sample carrying drum 1 can be immobilised by an external control 9 in the form of a sensitive key or push button operated switch for example. Stopping the drum makes it possible to fit or remove sample tubes during the measuring phases. The simplicity of the holding means ensures rapid and easy fitting. Indeed, the accuracy of measurement cannot be affected by short-term stoppages by virtue of the overall process time which is about two hours. The ease of handling, fitting and removing the sample tubes 3 provides the guarantee of not upsetting measurements which may be in progress.

The apparatus according to the invention has an observation window 10 connected to the sample carrying support by a casing 11 opening out in line with the support 1 through a slot 12 of small width close to the width of a tube 3 over the total height of the support. The casing 11 forms the connection between the support 1 which carries the samples and the analysis and stationary processing unit 13. It provides all the conditions of shielding of the samples from external light needed for visual examination of the samples by the analysis device 14. It will, of course, be understood that the containers or tubes 3 will have to be at least in part transparent for carrying out the visual examination of the liquid samples carried in the tubes 3.

The analysis device 14 is composed of a visual detection assembly 15 and an analysis and video transmission assembly 16. The former comprises a light emitter 17 concentrated on the observation slot 12. The image of this latter is formed by an objective lens 18 on image-forming means, such as a light-sensitive surface or support 19 of the charge transfer type.

According to the method of analysis and the form of sample carrier used, so that the light-sensitive surface or support 19 will be constituted by one or other type of charge coupling device or charge transfer device having cells known by the initials C.C.D.

In the version under consideration, which has a rotating support, the support could consist of a single bar 20, that is to say a linear arrangement of cells. Indeed, the tubes are scrutinised or detected one by one as they pass in front of the slot and only a difference in length between a linear light-coloured zone and a linear dark-coloured zone requires to be detected.

Exploration detection and image transmission are performed in the form of video signals after the fashion of a television camera.

In the case of a single bar, one might be satisfied with the forming of a simple image or direct observation through a simple slot-shaped diaphragm. To this end, the slot 12 may be sufficient.

Image acquisition and storage in a memory are carried out by a data assembly comprising a computer and identification unit 21 connected to the conventional peripheral assemblies of a data unit 22, display and monitoring screen 23, printer 24 and keyboard 25.

By virtue of the identification labels 7 carrying the customer code, the apparatus according to the invention makes it possible directly to print the results of the test on the customer sheet 26.

Figure 3:
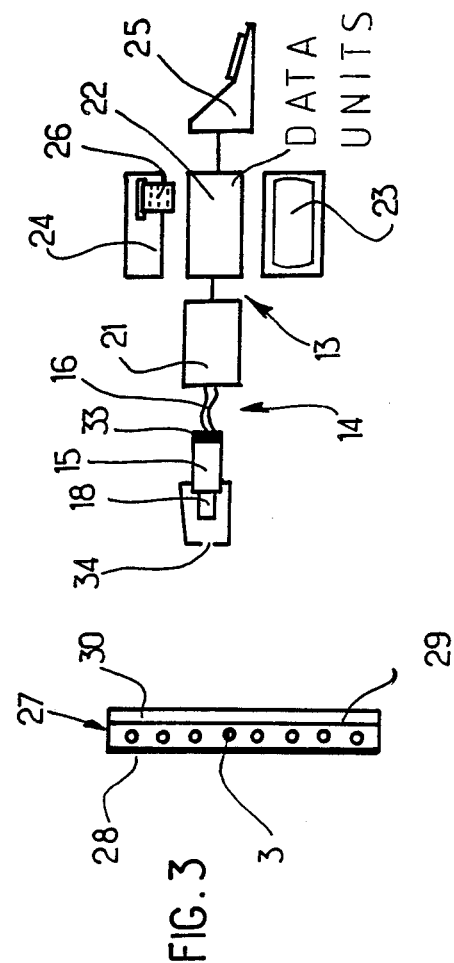
FIG. 3 is a detailed horizontal section showing the whole of a measuring apparatus having a fixed sample carrying support.

The alternative embodiment shown in FIG. 3 comprises a fixed specimen carrying support 27, for example in the form of a vertical flat member 28 provided with appropriate means of holding the tubes of samples 3 in a vertical position and, for example, in the form of top 29 and bottom 30 support bars. The bottom bar may have individual locations for coded identification labels 31.

Vertical supporting of each tube is guaranteed, for example, by grippers 32 or circular passages in a longitudinal element.

According to this form of embodiment, a matrix 33 of cells known by the initials C.C.D. may for example be formed on a flat sensitive element of the charge transfer type, by an objective lens or simply an optical diaphragm 34. Image detection is carried out by scanning and video transmission in the same way as with a television camera. The image acquisition and processing unit will operate according to a programme adapted to the manner of operation of that used in the rotary support version.

The data processing and result presentation chain is identical to that of the preceding version.

The measuring method employed by the apparatus according to the invention comprises the following main stages.

The sample tube is mounted on the sample carrying support 1. For this purpose, the support means with which it is provided ensure an appreciable saving on time. The self-adhesive label corresponding to the customer's code is affixed below the tube in the position provided where the identification is permanently fixed to the support. It then carries a position or serial code.

During this assembly time, the drum is immobilised by means of the key 9. This immobilisation, coupled with the measuring unit, suspends measurement during this setting-up time.

Indeed, upsets of a mechanical nature on the support arising from setting-up of the sample could only produce erroneous readings which could not be taken into account for purposes of the test.

The first pass or, in the case of the fixed specimen support version, the first time the specimen is placed in front of the observation window will give rise to the recording of a measuring sequence under references provided by the coded identification bale.

At each new presentation in front of the measuring window or at each new dwell time in the fixed support version the apparatus will register the height of the level of interphase or border between the light-coloured fraction of a relatively low or lesser density and the remaining fraction carrying particles or matter which or in the course of sedimentation below the light-coloured fraction.

The detection principle is based on the difference in light intensity between the upper part of the liquid and the volume containing the particles in course of sedimentation and of which the sedimentation rate is being examined.

This limit appears sufficiently clearly to allow precise measurement.

The image of the slot 12 or of the fixed support 27 is formed by the objective lens 18 on the light sensitive surface or support 19 which is of the charge transfer type either solely in a linear development in the case of a bar 20 or as a surface in the case of a C.C.D. matrix 33. In the first case, the codes are limited to those rendered by alternating light zones and dark zones or alternations of more or less extensive linear dark zones, of which the bar code is a typical example.

The identification code is registered at the first observation and is confirmed at every pass.

In the case of the version which has the rotary support the speed of rotation of the drum will not exceed a value which permits of adequate scrutiny and image acquisition.

It is necessary, however, for the number of revolutions per hour to be appropriate to the provision of a sufficient number of measurements for one or other measurement which might not be in a linear ratio to the former to be rejected.

In the fixed support version, measurement is carried out permanently at times determined by the operator.

The apparatus according to the invention offers a complete and automatic service between preparation of the sample tube and setting out of the results on a personal sheet. By this fact, the work of medical analysis laboratories is considerably improved and makes it possible to guarantee a result in which there are no measurement errors.

Figure 4:
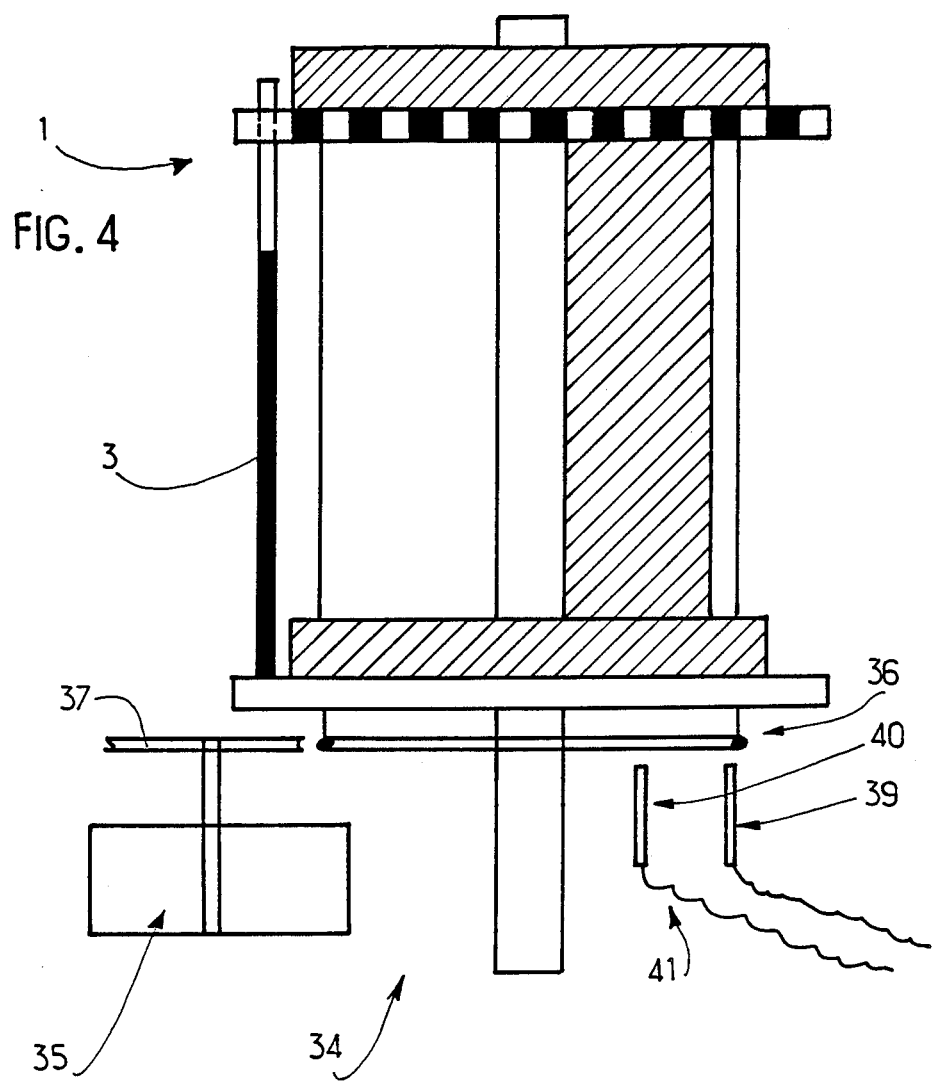
FIG. 4 is a diagrammatic cross-section showing the assembly for driving the rotating sample carrying support and the detection device and FIG. 5 is a plan view showing the configuration of the bottom web which makes it possible to detect original positions and positions at any given amount.
Figure 5:
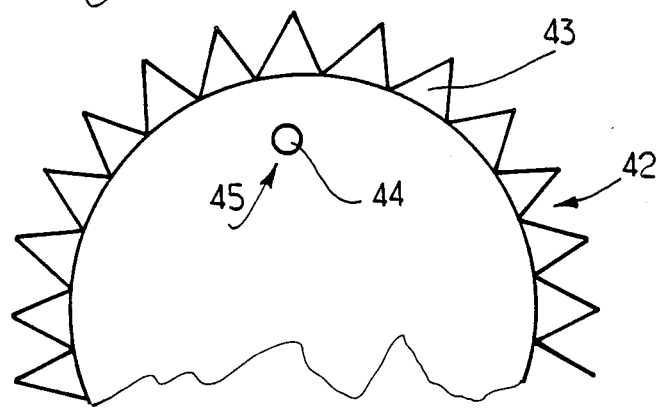

The drive assembly and the detection device will now be examined, reference being made to FIGS. 4 and 5 of the drawings.

The rotating support 1 is driven at the bottom by a drive assembly 34 consisting of an electric motor 35 operated by a microprocessor which is in kinematic communication with a drive disc 36 mounted rigidly on the drum shaft through a pulley 37. The rim of the disc 36 is provided with a rubber ring 38 which is in frictional contact with the groove in the pulley 37 in order to achieve a friction drive arrangement. The two drive means are capable of sliding and consequently of providing for an instant stop without damaging the drive assembly. Stops are vital and frequent for loading new samples.

The apparatus is automatically operated by a microprocessor programmed from two stationary position pickups 39 and 40, for example optical, of a double detection device 41. The first pick-up 39 is the original pick-up. It transmits the starting position and the sequence. The second pick-up 40 is a momentary position pick-up. It detects the position of the rotary support 1 at any given moment on the basis of variations in the light reflected on a crown-shaped zone 42 having teeth 43 at the level of the bottom web. Every change in reflected surface area between the teeth produces a variation in the reflected light and consequently a detection signal.

An aperture 44 constitutes the original visual reference point 45. It is sufficient to count the variations of reflected light and correlate them with the data relating to distance from point of origin in order to locate the position of the sample tubes 3 in relation to the point of origin given by the other pick-up.

Various obvious modifications and direct alternatives which entail no inventive contribution fall within the framework of the present invention.

I claim:

1. In a method of automatic determination of a sedimentation rate of liquids with the aid of a rotary support holding a plurality of containers in an upright position, at least some of said containers holding respective of said liquids therein, image-forming means for forming an image of a selected container, and processing means including a memory for processing the image of the selected container, each container being at least in part transparent, the liquid in each container containing particles in suspension, a border being defined between a lightly colored fraction of a liquid having a relatively low density, and the remaining fraction of the liquid in the respective containing carrying particles which are in the course of sedimentation, there occurring a difference in the light intensity between the lightly colored fraction and the remaining fraction, and wherein said border has a height which is dropping as a function of time, the steps comprising illuminating the selected container, rotating said rotary support repeatedly at regular intervals to a position wherein the selected of said containers is within view of said image-forming means, said containers being free of any vertical displacing movement, repeatedly forming the image of said fractions on said image-forming means at said regular time intervals, and determining said sedimentation rate by said processing means from said light intensity difference as a function of time.

2. The method as claimed in claim 1, further comprising the steps of identifying each container, and printing out the sedimentation rate for each identified container.

3. The method as claimed in claim 1, further comprising the step of at least momentarily stopping rotation of said rotary support while forming the image of said fractions on said image-forming means.

4. In a method of automatic determination of a sedimentation rate of liquids with the aid of a rotary support holding a plurality of containers in an upright position, at least some of said containers holding respective of said liquids therein, image-forming means for forming an image of a selected container, and processing means including a memory for processing the image of the selected container, each container being at least in part transparent, the liquid in each container containing particles in suspension, a border being defined between a lightly colored fraction of a liquid having a relatively low density, and the remaining fraction of the liquid in the respective container carrying particles which are in the course of sedimentation, there occurring a difference in the light intensity between the lightly colored fraction and the remaining fraction, and wherein said border has a height which is dropping as a function of time, the steps comprising illuminating the selected container, repeatedly making observations of said fractions and of said border in the selected container, the selected container being free of any vertical displacing movement, noting said observations, and determining said sedimentation rate from the noted observations.

5. An apparatus for continuous display of a particle sedimentation rate in a liquid, comprising in combination rotary support means adapted to hold a plurality of light-transparent containers, each container holding a liquid, means for selecting any container to be observed, at least a portion of a selected container being observable from the exterior, lighting means illuminating the selected container, image-forming means arranged to form an image of said at least portion of the selected container, and the liquid held therein, means on said image-forming means to create video signals from the so-formed image, computer means arranged to process said video signals, video signal transmission means transmitting said video signals from said image-forming means to said computer means, and display means for displaying the signals processed by said computer means.

6. The apparatus according to claim 5, further including identification means placed on said rotary support means for identifying respective of said containers, and wherein said display means includes a monitoring screen, a printer and a keyboard controlling said printer, so that the processed signals are printable on said printer.

7. The apparatus according to claim 5, further comprising means for correlating the processed signals with the container of which an image is formed by said image-forming means.

8. The apparatus according to claim 7, wherein said correlating means include a bottom web mounted on said rotary support means, said bottom web being formed with a peripheral crown-shaped zone including a ring having a plurality of reference marks, a stationary "detector of origin" pick-up for transmitting a starting position of said rotary support means, and a predetermined sequence of said rotary means, and a stationary position pick-up for detecting the position of of said rotary support means on the basis of variations of light reflected from said crown-shaped zone.

9. The apparatus according to claim 8, further including a microprocessor connected to, and programmed by said pick-ups.

10. The apparatus according to claim 8, wherein said starting position for said "detector of origin" is defined by an aperture formed in said ring, and wherein said reference marks include outwardly projecting teeth formed on said ring.

11. The apparatus according to claim 5, wherein said rotary support means has a cylindrical shape and is provided with a support ring formed with a plurality of recesses, said containers being supported in respective of said recesses.

12. The apparatus according to claim 5, wherein said image-forming means includes a bar containing a plurality of charge transfer cells.

13. The apparatus according to claim 5, wherein said image forming means includes a charge-coupled device (C.C.D) taking the form of a matrix of a plurality of light-sensitive diode cells.

14. The apparatus according to claim 5, further comprising a drive assembly for driving said rotary support means, and including an electric motor, a pulley mounted on a shaft of said electric motor, said pulley being formed with a peripheral groove, said rotary support means including a drive disc mounted on a shaft of said rotary support means, said drive disc having a rim fitted with a rubber ring, said rubber ring being in frictional contact with said peripheral groove formed in said pulley.

* * * * *